United States Patent [19]

Fuchs et al.

[11] 4,297,366
[45] Oct. 27, 1981

[54] COMBATING ARTHROPODS WITH 2,2-DIMETHYL-3-(2-FLUOROALKYL-2-OXY-VINYL)-CYCLOPROPANE-CARBOXYLIC ACID ESTERS

[75] Inventors: Rainer Fuchs, Wuppertal; Ingeborg Hammann, Cologne; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 142,928

[22] Filed: Apr. 23, 1980

[30] Foreign Application Priority Data

May 16, 1979 [DE] Fed. Rep. of Germany ....... 2919820

[51] Int. Cl.³ .................. A01N 53/00; C07C 69/743; C07C 121/75; C07D 209/34
[52] U.S. Cl. ................ 424/274; 260/326 A; 260/347.4; 260/465 D; 424/285; 424/304; 424/305; 424/308; 542/426; 560/65; 560/118; 560/124; 562/474; 562/500; 562/506; 568/663; 568/669; 568/685
[58] Field of Search ............ 260/465 D, 326 A, 347.4; 424/304, 305, 274, 285, 308; 560/124, 65, 118; 562/474, 500, 506; 568/663, 669, 685; 542/426

[56] References Cited

FOREIGN PATENT DOCUMENTS 1287080 1/1969 Fed. Rep. of Germany .
1926433 12/1969 Fed. Rep. of Germany .
2109010 9/1971 Fed. Rep. of Germany .
2230862 12/1972 Fed. Rep. of Germany .
2326077 1/1974 Fed. Rep. of Germany .
2356125 5/1974 Fed. Rep. of Germany .
2634663 3/1977 Fed. Rep. of Germany .
2650534 5/1978 Fed. Rep. of Germany .
2851428 6/1979 Fed. Rep. of Germany .
2907609 9/1979 Fed. Rep. of Germany .

Primary Examiner—Dolph H. Torrence
Attorney, Agent, or Firm—Sprung, Felfe, Horn, Lynch & Kramer

[57] ABSTRACT 2,2-Dimethyl-3-(2-fluoroalkyl-2-oxy-vinyl)-cyclopropane-carboxylic acid esters of the formula

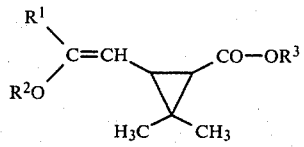

in which
 $R^1$ is fluoroalkyl,
 $R^2$ is an optionally substituted alkyl, cycloalkyl, aralkyl or aryl radical, and
 $R^3$ is a radical customary in the alcohol component of pyrethroids which possess arthropodicidal properties. New intermediates therefor are also shown.

10 Claims, No Drawings

COMBATING ARTHROPODS WITH 2,2-DIMETHYL-3-(2-FLUOROALKYL-2-OXY-VINYL)-CYCLOPROPANE-CARBOXYLIC ACID ESTERS

The invention relates to certain new fluorine-substituted oxyalkenyl-cyclopropanecarboxylic acid esters, to a process for their preparation and to their use as arthropodicides, especially as insecticides and acaricides.

It also relates to intermediates for the said preparative process.

It is known that certain alkenyl-cyclopropanecarboxylic acid esters, for example 3-(2-methyl-prop-1-enyl)-2,2-dimethyl-cyclopropane-1-carboxylic acid 3-phenoxy-benzyl ester and 3-(2,2-dichlorovinyl)-2,2-dimethylcyclopropane-1-carboxylic acid 3-phenoxybenzyl ester, have an insecticidal and acaricidal action (see DE-OS's (German Published Specifications) Nos. 1,926,433 and 2,326,077). However, the action of these compounds is not always satisfactory, especially in the case of low concentrations of active compounds and when small amounts are applied.

The present invention now provides:

(1), as new compounds, the fluorine-substituted oxyalkenylcyclopropanecarboxylic acid esters of the general formula

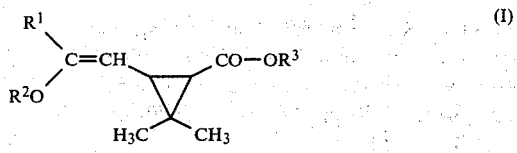

in which
 R$^1$ represents alkyl substituted by at least one fluoro substituent,
 R$^2$ represents an optionally substituted alkyl, cycloalkyl, aralkyl or aryl radical and
 R$^3$ represents a radical customary in the alcohol component of pyrethroids;

(2) a process for the preparation of a compound of the formula (I), characterized in that a fluorine-substituted oxyalkylenyl-cyclopropanecarboxylic acid of the general formula

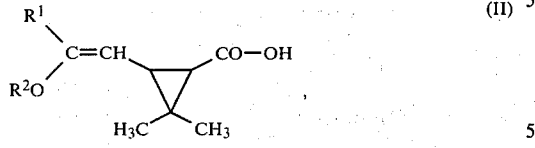

in which R$^1$ and R$^2$ have the meanings indicated above, or a reactive derivative thereof, is reacted with an alcohol of the general formula

in which R$^3$ has the meaning indicated above, or with a reactive derivative thereof, if appropriate in the presence of an acid acceptor and if appropriate using one or more diluents;

(3) the new fluorine-substituted oxyalkenyl-cyclopropanecarboxylic acids of the general formula

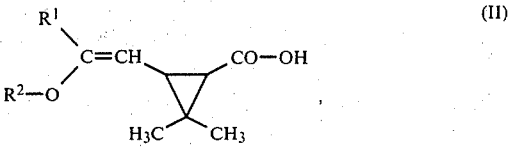

in which R$^1$ and R$^2$ have the meanings indicated under (1);

(4) a process for the preparation of a fluorine-substituted oxyalkenyl-cyclopropanecarboxylic acid of the formula (II), characterized in that a fluorine-substituted oxy-diene of the general formula

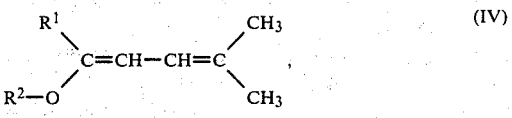

in which R$^1$ and R$^2$ have the meanings indicated under (1), is reacted with a diazoacetic acid ester of the general formula

in which R$^4$ represents C$_1$–C$_4$–alkyl, in the presence of a catalyst, and the ester prepared in this manner, of the general formula

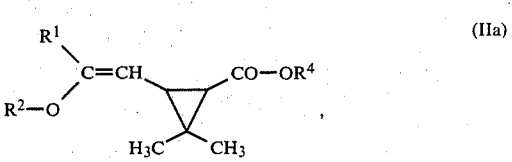

in which R$^1$, R$^2$ and R$^4$ have the meanings indicated above, is saponified by a customary method, by heating with an aqueous-alcoholic alkali metal hydroxide solution, to give the corresponding carboxylic acid of the formula (II);

(5) the new fluorine-substituted oxy-dienes of the general formula

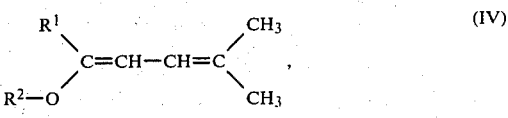

in which R$^1$ and R$^2$ have the meanings indicated under (1), and (6) a process for the preparation of a fluorine-substituted oxy-diene of the formula (IV), characterized in that a fluorine-substituted carboxylic acid ester of the general formula

in which R$^1$ and R$^2$ have the meanings indicated above, is reacted with 3-methyl-but-2-enyl-triphenyl-phosphonium bromide, of the formula

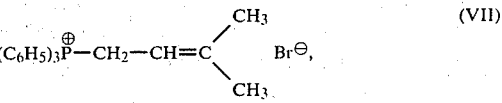

in the presence of a strong base and if appropriate using a diluent.

The fluorine-substituted oxyalkenyl-cyclopropanecarboxylic acid esters of the formula (I) are distinguished by a high insecticidal and acaricidal activity.

Surprisingly, the compounds of the formula (I) exhibit a considerably more powerful insecticidal and acaricidal action than compounds, known from the state of the art, of analogous structure and the same type of action.

Preferred compounds of the formula (I) are those in which $R^1$ represents $C_1-C_4$-fluoroalkyl or $C_1-C_4$-chlorofluoroalkyl, $R^2$ represents $C_1-C_4$-alkyl, $C_1-C_4$-halogenoalkyl, $C_5-C_6$-cycloalkyl or benzyl and $R^3$ represents one of the radicals below, which are customary in the alcohol component of pyrethroids:

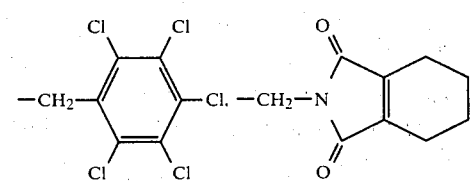

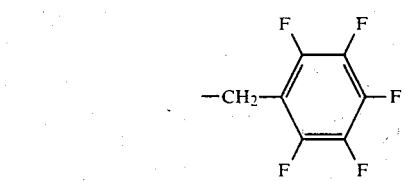

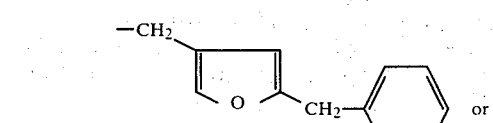

or

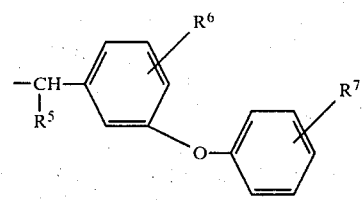

wherein $R^5$ represents hydrogen, cyano, ethynyl, methyl or ethyl and $R^6$ and $R^7$, which can be identical or different, represent hydrogen or halogen.

The general formula (I) also includes the various possible stereoisomers and optically active isomers, and mixtures thereof.

The compounds of the formula (I) are preferably prepared by a variant (a) of the process indicated under (2) above, by reacting, as reactive derivatives of the carboxylic acids of the formula (II), the corresponding carboxylic acid chlorides of the general formula

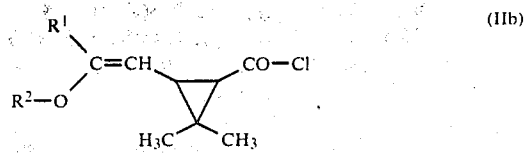

in which $R^1$ and $R^2$ have the meanings indicated under (1), with alcohols of the formula (III) above, if appropriate in the presence of an acid acceptor and if appropriate using a diluent.

The compounds of the formula (I) in which $R^3$ represents optionally halogen-substituted 3-phenoxy-α-cyanobenzyl are particularly preferably prepared by a process variant (b), by reacting carboxylic acid chlorides of the formula (IIb) above with optionally halogen-substituted 3-phenoxy-benzaldehydes of the general formula

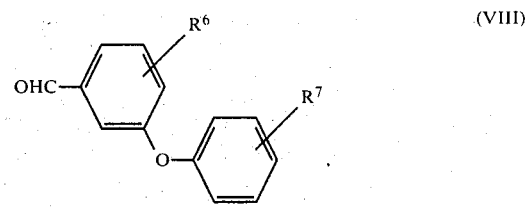

in which $R^6$ and $R^7$ have the meanings indicated above, and at least an equimolar amount of alkali metal cyanide (preferably sodium cyanide or potassium cyanide), if appropriate in the presence of a catalyst and if appropriate using a diluent.

If 3-(2-methoxy-3,3,3-trifluoro-prop-1-enyl)-2,2-dimethyl-cyclopropane-1-carboxylic acid chloride and 3-phenoxy-benzyl alcohol, for example, are used as starting substances in process variant (a) and 3-(2-ethoxy-3,3,3-trifluoro-prop-1-enyl)-2,2-dimethyl-cyclopropane-1-carboxylic acid chloride, sodium cyanide and 4-fluoro-3-phenoxy-benzaldehyde are used as starting substances in variant (b), the corresponding reactions can be outlined by the following equations:

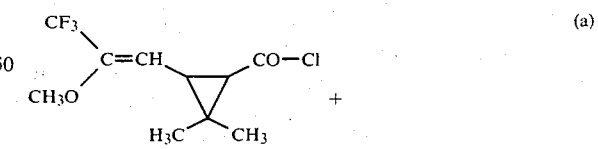

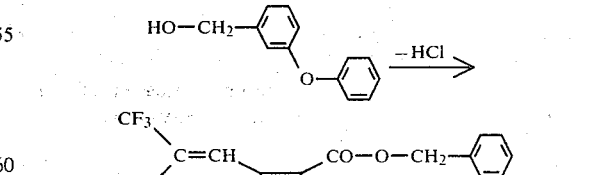

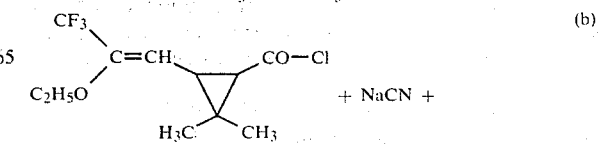

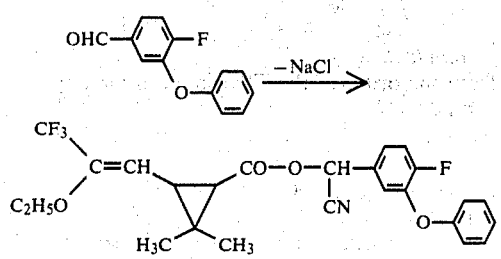

All variants of the process for the preparation of the fluorine-substituted oxyalkenyl-cyclopropanecarboxylic acid esters (I) are preferably carried out using a suitable solvent or diluent. Possible solvents or diluents are virtually any of the inert organic solvents. These include, as preferences, aliphatic and aromatic, optionally chlorinated hydrocarbons, such as pentane, hexane, heptane, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

When the reaction is carried out in a two phase medium, water is used as the second solvent component.

Acid acceptors which can be used in variant (a) of the preparative process described under (2) are any of the customary acid-binding agent. Acid-binding agents which have proved particularly suitable are alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine and pyridine.

Compounds which usually serve as auxiliaries for the phase transfer of reactants in reactions in multiphase media are, in general, used as catalysts in variant (b) of process (2). Tetraalkyl- and trialkylaralkylammonium salts, for example tetrabutylammonium bromide and trimethyl-benzylammonium chloride, may be mentioned in particular.

The reaction temperature can be varied within a substantial range. In general, the reaction is carried out between 0° and 100° C., preferably between 10° and 50° C. in process variant (a) and preferably between 10° and 30° C. in variant (b).

In general, all variants of the process according to the invention are carried out under normal pressure.

The starting substances are usually employed in equimolar amounts for carrying out process (2) according to the invention. An excess of one or the other of the reactants brings no substantial advantages. The reaction is in general carried out in one or more diluents in the presence of an acid acceptor or a catalyst, and the reaction mixture is stirred at the required temperature for several hours. The reaction mixture is then shaken with toluene/water and the organic phase is separated off, washed with water and dried. After distilling off the solvent in vacuo, the new compounds are in general obtained in the form of oils, some of which cannot be distilled without decomposition, but are freed from the last volatile constituents by so-called "incipient distillation", that is to say by prolonged heating to moderately elevated temperatures under reduced pressure, and are purified in this manner. The refractive index is used for their characterization.

The formulae (II), (IIa), (IIb), (III), (IV), (V), (VI), (VII) and (VIII) provide definitions of the starting substances for the preparation of the compounds according to the invention. Preferably, in these formulae, $R^1$ to $R^3$ and $R^5$ to $R^7$ have those meanings which have already been mentioned as preferred in connection with the compounds of the formula (I), and $R^4$ represents $C_1$-$C_4$-alkyl.

Alcohols of the formula (III), and aldehydes of the formula (VIII) as compounds to be derived therefrom, which are to be employed as reactants in the process indicated under (2) for the preparation of the fluorine-substituted oxyalkenyl-cyclopropanecarboxylic acid esters of the formula (I) are known (see DE-OS's (German Published Specifications) Nos. 2,005,489, 2,326,077 and 2,709,264; and British Patent Specification 1,078,511).

Examples which may be mentioned are: tetrahydrophthalimidomethyl alcohol, pentafluorobenzyl alcohol, pentachlorobenzyl alcohol, 5-benzyl-3-furyl alcohol, 3-phenoxy-benzylalcohol, 3-phenoxy-benzaldehyde, 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-benzyl alcohol, 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-α-cyano-benzyl alcohol, 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-α-ethynyl-benzyl alcohol, 3-phenoxy-4-fluoro-α-methyl-benzyl alcohol and 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-benzaldehyde.

The fluorine-substituted oxyalkenyl-cyclopropanecarboxylic acids (II), and the corresponding esters (IIa) and corresponding acid chlorides (IIb) as reactive derivatives thereof, to be used as starting compounds have not hitherto been described in the literature.

Carboxylic acid chlorides of the formula (IIb) can be prepared by customary methods from the corresponding carboxylic acids of the formula (II), by reaction with a chlorinating agent, for example thionyl chloride, if appropriate using a diluent, for example carbon tetrachloride, at a temperature between 10° and 100° C.

The carboxylic acids of the formula (II) are obtained from the corresponding alkyl esters of the formula (IIa) by heating to a temperature between 50° and 150° C. with an aqueous-alcoholic alkali metal hydroxide solution, for example sodium hydroxide solution, for several hours. The mixture is worked up by customary methods, for example by distilling off the alcohol, diluting the product phase with water, acidifying and extracting the mixture with methylene chloride, drying the organic extracts and distilling off the solvent.

The fluorine-substituted oxyalkenyl-cyclopropanecarboxylic acid esters of the formula (IIa) are obtained, as illustrated above, under (4), by reacting fluorine-substituted oxy-dienes of the formula (IV) above with diazoacetic acid esters of the formula (V) above in the presence of a catalyst, at a temperature between 50° and 200° C., preferably between 80° and 150° C. The catalysts used are preferably copper, copper compounds or mixtures of copper and copper compounds, for example copper powder and copper sulphate.

For working up, the reaction mixture is diluted with methylene chloride and filtered. The solvent is stripped off from the filtrate, after washing with water and drying, and the crude product which remained is purified if necessary, by distillation under reduced pressure.

Examples which may be mentioned of the carboxylic acids of the formula (II) and the corresponding esters (IIa) and acid chlorides (IIb) are: 3-(2-methoxy-3,3,3-trifluoro-prop-1-enyl)-, 3-(2-ethoxy-3,3,3-trifluoro-prop-1-enyl)-3-(2-n-propoxy-3,3,3-trifluoro-prop-1-enyl)-, 3-(2-iso-propoxy-3,3,3-trifluoro-prop-1-enyl)- and 3-(2-(2-chloro-ethoxy)-3,3,3-trifluoro-prop-1-enyl)-2,2-dimethyl-cyclopropane-1-carboxylic acid and the corresponding acid chlorides, methyl esters and ethyl esters.

The new fluorine-substituted oxy-dienes of the formula (IV) defined above, under (5), are obtained as indicated above, under (6), by reacting fluorine-substituted carboxylic acid esters of the formula (VI) above with 3-methyl-but-2-enyl-triphenyl-phosphonium bromide in the presence of a strong base, for example butyl-lithium, using a diluent, for example tetrahydrofuran and hexane, at a temperature between $-70°$ and $+100°$ C., preferably between $-20°$ and $+50°$ C.

For working up, the reaction mixture is diluted with water and extracted several times with a water-immiscible solvent, for example petroleum ether. The solvent is stripped off from the combined extracts, after drying. The crude product which remains in the residue is purified if necessary, by vacuum distillation.

Examples of the fluorine-substituted oxy-dienes of the formula (IV) which may be mentioned are: 1,1,1-trifluoro-2-methoxy-5-methyl-hexa-2,4-diene, 1,1,1-trifluoro-2-ethoxy-5-methyl-hexa-2,4-diene, 1,1,1-trifluoro-2-n-propoxy-5-methyl-hexa-2,4-diene, 1,1,1-trifluoro-2-iso-propoxy-5-methyl-hexa-2,4-diene and 1,1,1-trifluoro-2-(2-chloro-ethoxy)-5-methyl-hexa-2,4-diene.

Fluorine-substituted carboxylic acid esters of the formula (VI) which are to be used as starting substances for the process indicated under (6) are known (see J.Am.Chem.Soc. 69 (1947), 1,819).

Examples which may be mentioned are trifluoroacetic acid methyl ester, ethyl ester, n-propyl ester and iso-propyl ester.

3-Methyl-but-2-enyl-triphenylphosphonium bromide (VII) is likewise known (see Helv. Chim. Acta 44 (1961), 998-9).

As already mentioned, the new fluorine-substituted oxyalkenyl-cyclopropanecarboxylic acid esters (I) are distinguished by a high insecticidal and acaricidal activity. They can be employed against insects and mites which are harmful to plants, in agriculture and forestry and in the protection of stored products and the hygiene field, and against ectoparasites, in the field of veterinary medicine.

The active compounds are well tolerated by plants, have a flavorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentials* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans; from the order of the* Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture wth a liquid diluent or carrier containing a surfactant.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The pesticidal activity of the compounds of this invention is illustrated by the following examples wherein the compounds according to the present invention are each identified by the number (given in brackets) from the preparative Example, which will be found later in this specification.

The preparation of the novel compounds is shown in the following illustrative examples:

EXAMPLE 1

The compounds of the formula (IV) could be prepared for example, as follows:

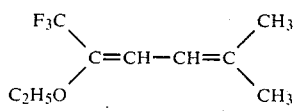

96 ml of a 20% strength solution of n-butyl-lithium in hexane were added dropwise to a suspension of 82.2 g (0.2 mol) of dry 3,3-dimethylallyl-triphenylphosphonium bromide in 300 ml of anhydrous tetrahydrofuran at 0° C. under nitrogen, while stirring. The deep red solution thus obtained was stirred at 0° C. for a further 15 minutes and 28.4 g (0.2 mol) of trifluoroacetic acid ethyl ester were then added dropwise at 0°–10° C. The mixture was then stirred at room temperature until it was almost decolorized (about 12 hours). 600 ml of water were then added to the reaction mixture and the mixture was extracted 5 times with 200 ml of petroleum ether each time. The petroleum ether phases were dried over magnesium sulphate and the solvent was then stripped off in a rotary evaporator under a waterpump vacuum. 150 ml of n-hexane were added to the residue and the mixture was then filtered. The solvent was subsequently distilled off from the filtrate under normal pressure and the oily residue was then distilled in vacuo. 16.2 g (41.8% of theory) of 1,1,1-trifluoro-2-ethoxy-5-methyl-2,4-hexadiene were obtained as a slightly yellowish liquid with a boiling point of 72° C./36 mbar.

The following compounds were obtained analogously:

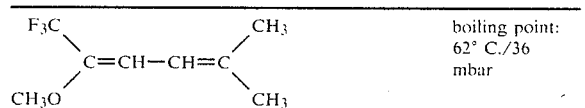

boiling point: 62° C./36 mbar

| | |
|---|---|
| iso-C₃H₇O\C=CH—CH=C/CH₃ (F₃C, CH₃) | boiling point: 83° C./36 mbar |
| Cl—CH₂—CH₂—O\C=CH—CH=C/CH₃ (F₃C, CH₃) | boiling point: 62–63° C./4 mbar |
| n-C₃H₇O\C=CH—CH=C/CH₃ (F₃C, CH₃) | boiling point 92–93° C./36 mbar |
| CH₃O\C=CH—CH=C/CH₃ (F₃C—F₂C, CH₃) | boiling point: 73–74° C./36 mbar |
| C₂H₅O\C=CH—CH=C/CH₃ (F₃C—F₂C—F₂C, CH₃) | boiling point: 86–87° C./36 mbar |

EXAMPLE 2

The compounds of the formula (IIa) could be prepared, for example, as follows:

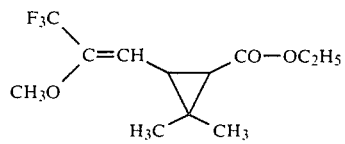

A mixture of 36 g (0.2 mol) of 1,1,1-trifluoro-2-methoxy-5-methyl-2,4-hexadiene, 1.2 g of copper powder and 1.5 g of copper sulphate (anhydrous) was heated to 110°–120° C. and a mixture of 18 g (0.1 mol) of 1,1,1-trifluoro-2-methoxy-5-methyl-2,4-hexadiene and 34.2 g (0.3 mol) of diazoacetic acid ethyl ester was then very slowly added dropwise in the course of 6 hours, also at 110°–120° C. while stirring. When the evolution of nitrogen had ended, the mixture was cooled, diluted with 500 ml of methylene chloride and then filtered. The filtrate was extracted by shaking with 500 ml of water and the organic phase was then separated off and dried over magnesium sulphate and the solvent was then distilled off under a waterpump vacuum. The oily residue was distilled in vacuo. Two fractions were thereby obtained:

Fraction 1: boiling point: 62°–65° C./36 mbar
Fraction 2: boiling point: 50°–85° C./2 mbar Fraction 1 (16.6 g) proved to be unreacted 1,1,1-trifluoro-2-methoxy-5-methyl-2,4-hexadiene. Fraction 2 was distilled again. 17.2 g (21.6% of theory) of 2,2-dimethyl-3-(3,3,3-trifluoro-2-methoxy-prop-1-enyl)-cyclopropanecarboxylic acid ethyl ester (isomer mixture) were obtained as a colorless liquid with a boiling point of 80°–82° C./2 mbar.

The following compounds were obtained analogously:

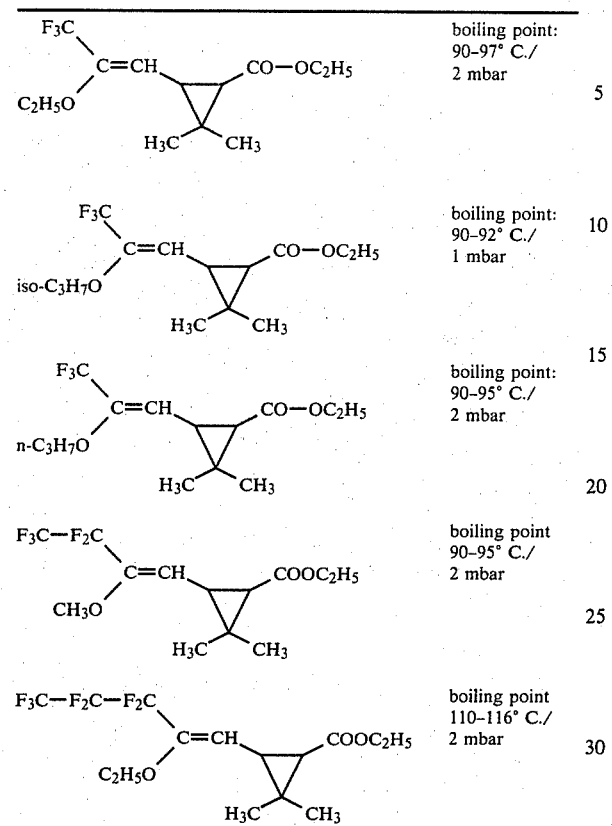

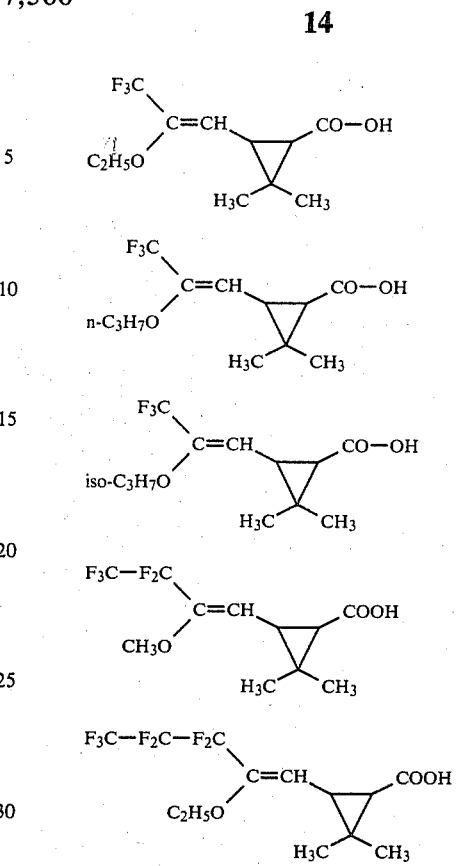

EXAMPLE 3

The starting compounds of the formula (II) could be prepared, for example, as follows:

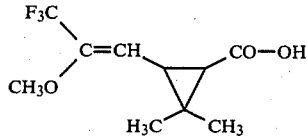

16.6 g (0.0624 mol) of 2,2-dimethyl-3-(3,3,3-trifluoro-2-methoxy-prop-1-enyl)-cyclopropanecarboxylic acid ethyl ester were dissolved in 100 ml of ethanol, a solution of 2.9 g (0.073 mol) of sodium hydroxide in 75 ml of water was then added and the mixture was heated to the reflux temperature for 4 hours, while stirring. The ethanol was then distilled off under a waterpump vacuum, the residue was taken up in 300 ml of water and the aqueous mixture was extracted once with 300 ml of methylene chloride. The aqueous phase was separated off, acidified with concentrated hydrochloric acid and then extracted twice with 300 ml of methylene chloride. The organic phase was then separated off over magnesium sulphate, dried and the solvent was distilled off under a waterpump vacuum. Last residues of solvent were removed by brief incipient distillation at a bath temperature of 50° C. under 2 mbar. 9 g (60.6% of theory) of 2,2-dimethyl-3-(3,3,3-trifluoro-2-methoxy-prop-1-enyl)-cyclopropanecarboxylic acid were then obtained as a yellow viscous oil.

The following compounds were obtained analogously:

EXAMPLE 4

The starting compounds of the formula (IIb) could be prepared, for example, as follows:

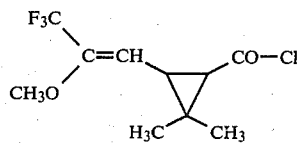

8.7 g (0.0365 mol) of 2,2-dimethyl-3-(3,3,3-trifluoro-2-methoxy-prop-1-enyl)-cyclopropanecarboxylic acid were dissolved in 100 ml of carbon tetrachloride, and 21 g of thionyl chloride were slowly added dropwise at 60° C., while stirring. The mixture was then heated to the reflux temperature for 4 hours. After this reaction time, excess thionyl chloride and carbon tetrachloride were distilled off under a waterpump vacuum. The residue was distilled in vacuo. 6 g (64.2% of theory) of 2,2-dimethyl-3-(3,3,3-trifluoro-2-methoxy-prop-1-enyl)-cyclopropanecarboxylic acid chloride were obtained as a slightly yellow liquid with a boiling point of 80° C./2 mbar.

The following compounds were obtained analogously:

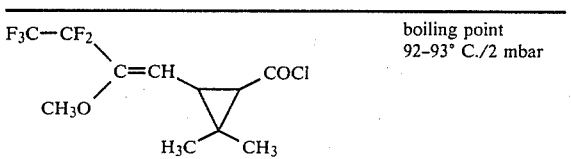

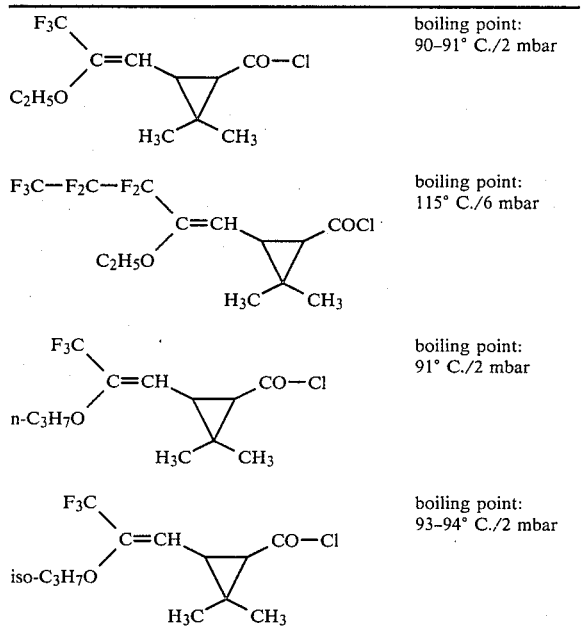

| | boiling point: 90–91° C./2 mbar |
| | boiling point: 115° C./6 mbar |
| | boiling point: 91° C./2 mbar |
| | boiling point: 93–94° C./2 mbar |

EXAMPLE 5

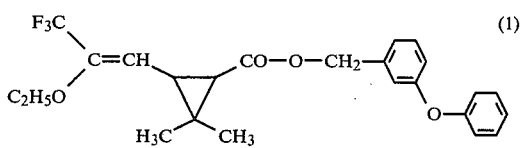 (1)

5.2 g (0.026 mol) of 3-phenoxy-benzyl alcohol and 7 g (0.026 mol) of 2,2-dimethyl-3-(3,3,3-trifluoro-2-ethoxy-prop-1-enyl)-cyclopropanecarboxylic acid chloride were dissolved in 100 ml of anhydrous toluene, and 2.5 g of pyridine, dissolved in 20 ml of anhydrous toluene, were added dropwise at 20°–25° C., while stirring. Stirring was then continued at 25°–35° C. for 3 hours. The reaction mixture was poured into 150 ml of water, to which 10 ml of concentrated hydrochloric acid were added, and the organic phase was separated off and washed again with 100 ml of water. The toluene phase was then dried over sodium sulphate and the solvent was distilled off under a water-pump vacuum. Last residues of solvent were removed by brief incipient distillation at a bath temperature of 60° C./1 mm Hg. 9.9 g (87.7% of theory) of 2,2-dimethyl-3-(3,3,3-trifluoro-2-ethoxy-prop-1-enyl)-cyclopropanecarboxylic acid 3-phenoxybenzyl ester were obtained as a yellow oil with the refractive index $n_D^{25}$: 1.5130.

EXAMPLE 6

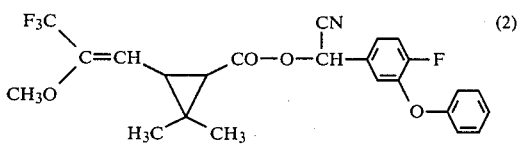 (2)

4.63 g (0.0214 mol) of 3-phenoxy-4-fluoro-benzaldehyde and 5.5 g (0.0214 mol) of 2,2-dimethyl-3-(3,3,3-trifluoro-2-methoxy-prop-1-enyl)-cyclopropanecarboxylic acid chloride were together added dropwise to a mixture of 1.7 g of sodium cyanide, 2.5 ml of water, 100 ml of n-hexane and 0.5 g of tetrabutylammonium bromide at 20°–25° C., while stirring, and the mixture was then stirred at 20°–25° C. for 4 hours. 300 ml of toluene were then added to the reaction mixture and the mixture was extracted by shaking twice with 300 ml of water each time. The organic phase was separated off and dried over magnesium sulphate and the solvent was distilled off under a waterpump vacuum. Last residues of solvent were removed by brief incipient distillation at a bath temperature of 60° C./1 mm Hg. 7.4 g (74.7% of theory) of 2,2-dimethyl-3-(3,3,3-trifluoromethyl-2-methoxy-prop-1-enyl)-cyclopropanecarboxylic acid 3-phenoxy-4-fluoro-α-cyano-benzyl ester were obtained as a viscous oil with the refractive index $n_D^{22}$: 1.5253.

The following compounds could be prepared analogously to Examples 5 and 6:

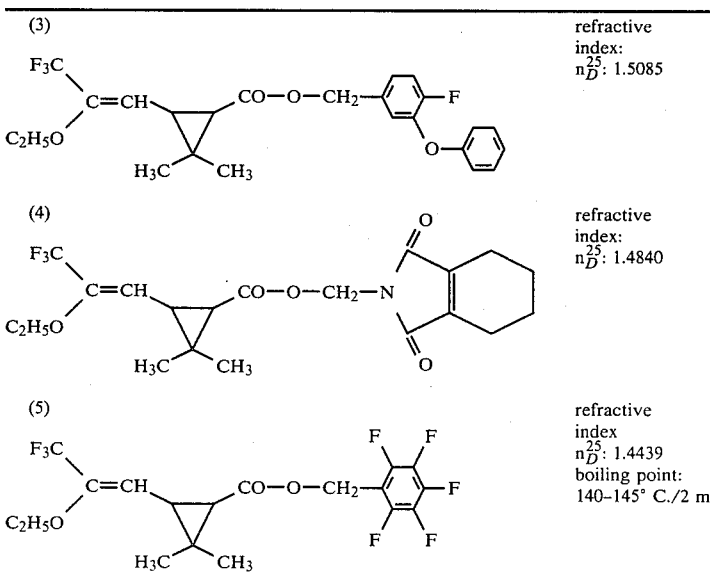

(3) refractive index: $n_D^{25}$: 1.5085

(4) refractive index: $n_D^{25}$: 1.4840

(5) refractive index $n_D^{25}$: 1.4439 boiling point: 140–145° C./2 mm Hg

-continued
(6)
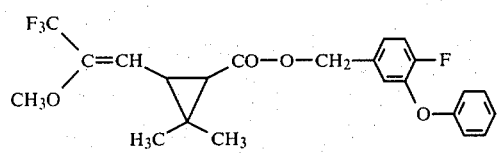
(7)
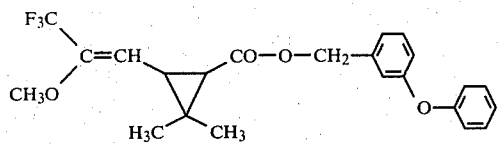
(8)
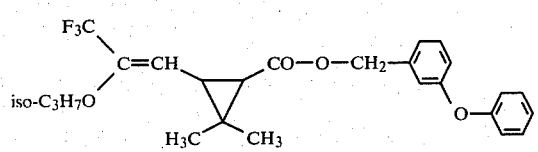
(9)
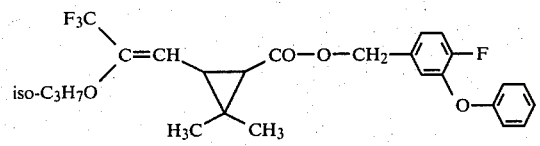
(10)
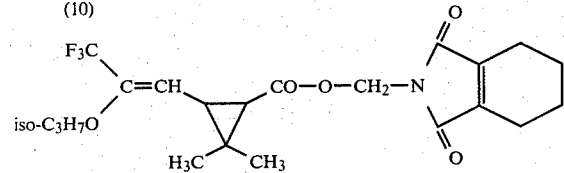
(11)
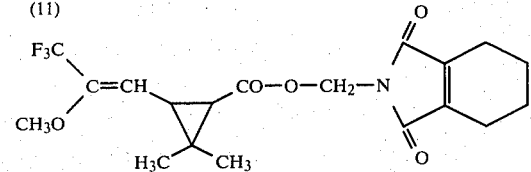
(12)
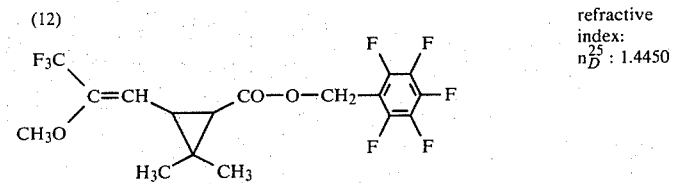
refractive index:
$n_D^{25}$ : 1.4450
(13)
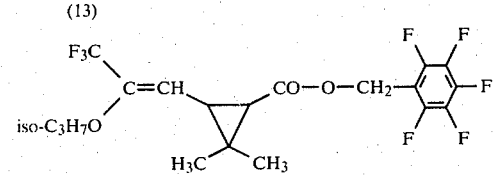

-continued
(14)
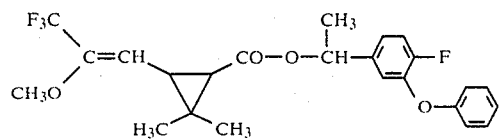
(15)
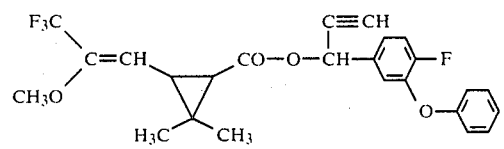
(16)
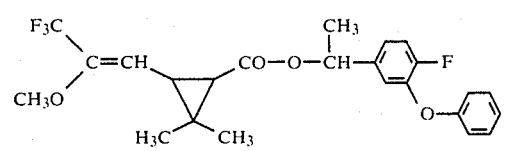
(17)
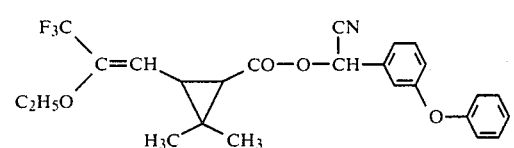
(18)
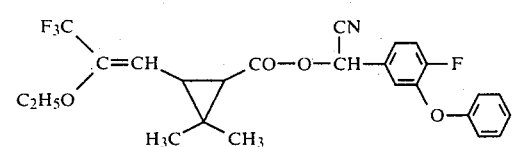
(19)
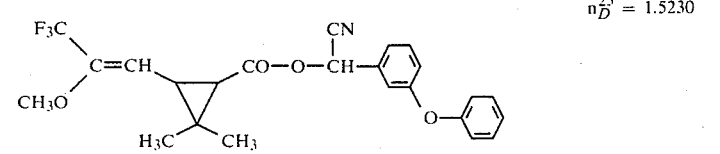
refractive index:
$n_D^{25} = 1.5230$
(20)
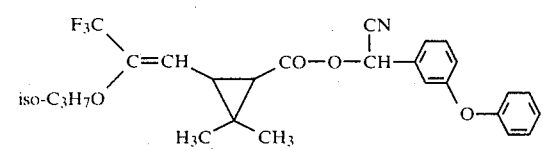
(21)
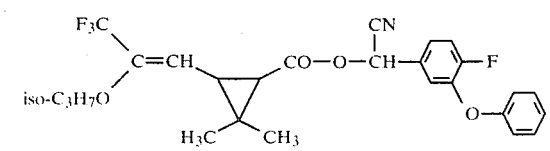

-continued
(22)
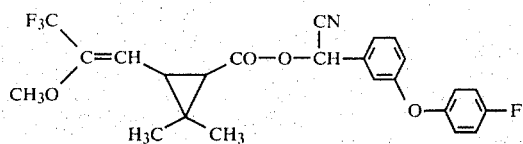
(23)
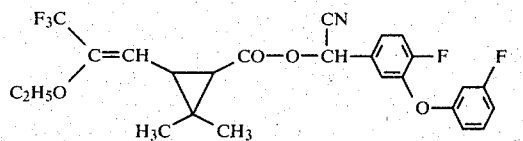
(24) refractive index: $n_D^{25}$: 1.5130
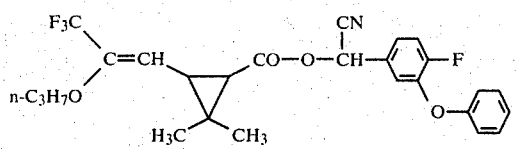
(25) refractive index: $n_D^{25}$: 1.5195
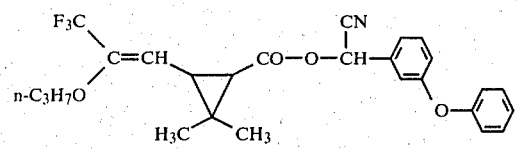
(26) refractive index: $n_D^{25}$: 1.5070
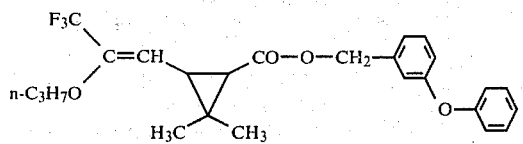
(27)
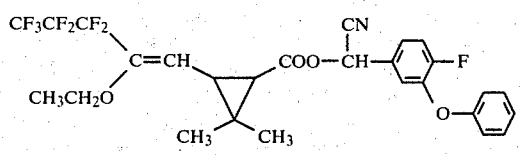
(28)
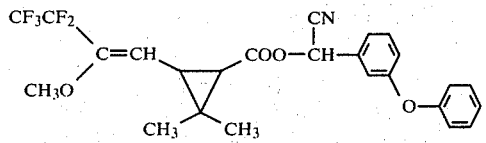
(29)
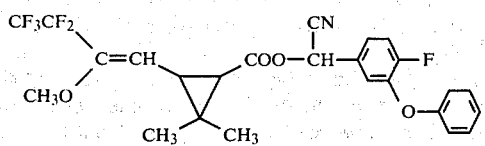
EXAMPLE 7
Plutella test
Solvent: 3 parts by weight of acetone
Emulsifier: 1 part by weight of alkylaryl polyglycol ether
To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into a preparation of active compound and were infested with caterpillars of the diamond-back moth (*Plutella maculipennis*), as long as the leaves were still moist.

After the specified periods of time, the degree of destruction was determined as a percentage: 100% meant that all of the caterpillars were killed whereas 0% meant that none of the caterpillars were killed.

In this test, for example, the following compounds showed a superior activity compared with the prior art: (1) and (3).

EXAMPLE 8

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared with the prior art: (17) and (18).

EXAMPLE 9

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compounds showed a superior activity compared with the prior art: (17), (18) and (3).

EXAMPLE 10

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared with the prior art: (18), (17) and (3).

EXAMPLE 11

$LT_{100}$ test for Diptera

Test insects: *Aedes aegypti*
Number of test insects: 25
Solvent: Acetone

The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was continuously observed. The time which was necessary for 100% "knock-down" was determined.

In this test, for example, the following compounds showed a superior action compared to the prior art: (17) and (18).

EXAMPLE 12

$LT_{100}$ test for Diptera

Test insects: *Musca domestica*, resistant
Number of test insects: 25
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was continuously observed. The time which was necessary for 100% "knock-down" was determined.

In this test, for example, the following compounds showed a superior action compared with the prior art: (17) and (18).

EXAMPLE 13

Test insects: *Sitophilus granarius*
Number of test animals: 25
Solvent: Acetone The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was observed 3 days after the commencement of the experiments. The destruction, in %, was determined. 100% denoted that all of the test insects had been killed; 0% denoted that none of the test insects had been killed.

In this test, for example, the following compounds showed a superior action compared with the prior art: (17) and (18).

EXAMPLE 14

Test with *Boophilus microplus* resistant

Solvent: 35 parts by weight of ethylene glycol monomethyl ether 35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult specimens of *Boophilus microplus* res. were immersed for 1 minute in the active compound preparation to be tested. After transfer to plastic beakers and storage in a climatically controlled chamber, the degree of destruction was determined.

In this test, for example, the following compounds from the preparative examples showed a superior action compared to the prior art: (1), (3), (17) and (18).

It will be appreciated that the instant specification and examples are set forth by way of illustration and not limitation, and that various modifications and changes may be made without departing from the spirit and scope of the present invention.

We claim:

1. A 2,2-dimethyl-3-(2-fluoroalkyl-2-oxy-vinyl)-cyclopropanecarboxylic acid ester of the formula in which
$R^1$ is $C_1$-$C_4$-fluoroalkyl or $C_1$-$C_4$-chlorofluoroalkyl,
$R^2$ is $C_1$-$C_4$-alkyl, $C_1$-$C_4$-halogenoalkyl, $C_5$-$C_6$-cycloalkyl or benzyl,
$R^3$ is $R^5$ is hydrogen, cyano, ethynyl, methyl or ethyl, and $R^6$ and $R^7$ each independently is hydrogen or halogen.

2. A compound according to claim 1, wherein such compound is 2,2-dimethyl-3-(3,3,3-trifluoro-2-ethoxy-prop-1-enyl)-cyclopropane-carboxylic acid 3-phenoxy-benzyl ester of the formula 3. A compound according to claim 1 wherein such compound is 2,2-dimethyl-3-(3,3,3-trifluoro-2-ethoxy-prop-1-enyl)-cyclopropane-carboxylic acid 3-phenoxy-4-fluorobenzyl ester of the formula 4. A compound according to claim 1, wherein such compound is 2,2-dimethyl-3-(3,3,3-trifluoro-2-ethoxy-prop-1-enyl)-cyclopropane-carboxylic acid 3-phenoxy-α-cyano-benzyl ester of the formula

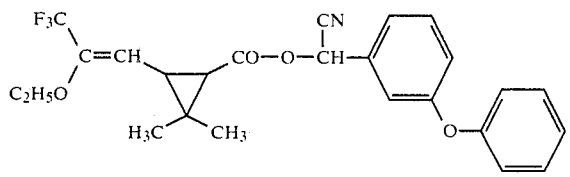

5. A compound according to claim 1, wherein such compound is 3,3-dimethyl-3-(3,3,3-trifluoro-2-ethoxy-prop-1-enyl)-cyclopropane-carboxylic acid 3-phenoxy-4-fluoro-α-cyano-benzyl ester of the formula

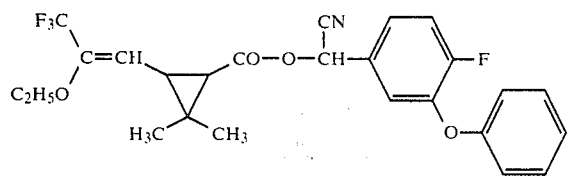

6. An arthropodicidal composition containing as active ingredient an arthropodicidally effective amount of a compound according to claim 1 in admixture with a diluent.

7. A method of combating arthropods which comprises applying to the arthropods, or to a habitat thereof, an arthropodicidally effective amount of a compound according to claim 1.

8. The method according to claim 7, in which said compound is 2,2-dimethyl-3-(3,3,3-trifluoro-2-ethoxy-prop-1-enyl)-cyclopropane-carboxylic acid 3-phenoxybenzyl ester, 2,2-dimethyl-3-(3,3,3-trifluoro-2-ethoxy-prop-1-enyl)-cyclopropane-carboxylic acid 3-phenoxy-4-fluorobenzyl ester, 2,2-dimethyl-3-(3,3,3-trifluoro-2-ethoxy-prop-1-enyl)-cyclopropane-carboxylic acid 3-phenoxy-α-cyanobenzyl ester, or 2,2-dimethyl-3-(3,3,3-trifluoro-2-ethoxy-prop-1-enyl)-cyclopropane-carboxylic acid 3-phenoxy-4-fluoro-α-cyano-benzyl ester.

9. A 2,2-dimethyl-3-(2-fluoroalkyl-2-oxy-vinyl)-cyclopropane carboxylic acid of the formula

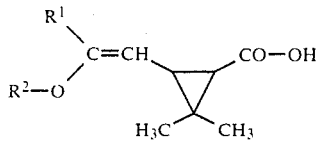

in which
$R^1$ is $C_1$-$C_4$-fluoroalkyl,
$R^2$ is $C_1$-$C_4$-alkyl, $C_1$-$C_4$-halogenoalkyl, $C_5$-$C_6$-cycloalkyl or benzyl.

10. A 2-methyl-5-oxy-2,4-pentadiene of the formula

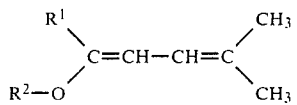

in which
$R^1$ is $C_1$-$C_4$-fluoroalkyl,
$R^2$ is $C_1$-$C_4$-alkyl, $C_1$-$C_4$-haloenoalkyl, $C_5$-$C_6$-cycloalkyl or benzyl.

* * * * *